United States Patent [19]

Nakane et al.

[11] Patent Number: 5,182,103
[45] Date of Patent: Jan. 26, 1993

[54] MAGNESIUM ALUMINOMETASILICATE COATED COMPOSITE POWDER AND USE THEREOF

[75] Inventors: Toshihiko Nakane, Yokohama; Masumi Koishi, Sagamihara; Hiroshi Fukui, Yokohama; Yutaka Okunuki, Yokohama; Yoshio Yahata, Yokohama; Shigenori Kumagai, Yokohama; Hiroyuki Yokoyama, Yokohama; Eiichiro Yagi, Yokohama; Minoru Fukuda, Yokohama; Tadao Ohta, Yokohama; Fujihiro Kanda, Yokohama; Kazuhisa Ohno, Yokohama; Toshihide Ebisawa, Yokohama; Tomiyuki Nanba, Yokohama; Susumu Takada, Yokohama; Masato Hatao, Yokohama; Masaru Suetsugu, Yokohama; Toshihiro Tanaka, Yokohama; Osamu Moro, Yokohama, all of Japan

[73] Assignee: Shiseido Company, Ltd., Tokyo, Japan

[21] Appl. No.: 361,880

[22] Filed: Jun. 6, 1989

Related U.S. Application Data

[63] Continuation-in-part of Ser. No. 357,616, May 24, 1989, abandoned, and a continuation of Ser. No. 939,379, Dec. 8, 1986, abandoned.

[30] Foreign Application Priority Data

| Dec. 9, 1985 | [JP] | Japan | 60-276505 |
| Jul. 22, 1986 | [JP] | Japan | 61-172499 |
| Nov. 21, 1986 | [JP] | Japan | 61-278374 |
| Jun. 7, 1988 | [JP] | Japan | 63-138311 |

[51] Int. Cl.$^5$ .............................................. A61K 31/78
[52] U.S. Cl. ............................ 424/78.03; 424/78.31; 424/78.24; 424/49; 424/68; 424/404; 514/951
[58] Field of Search ................... 424/401, 404, 78.24, 424/69, 64, 55, 68, 76.1, 76.21, 76.2, 78.31, 49, 68, 78.03; 514/951

[56] References Cited

U.S. PATENT DOCUMENTS

4,537,913 8/1985 Bauman ............................. 528/260
4,669,492 6/1987 Kleinsorgen ................. 428/DIG. 5

FOREIGN PATENT DOCUMENTS

53-136626 2/1978 Japan.
57-81823 5/1982 Japan.

OTHER PUBLICATIONS

Chemical Abstracts, vol. 89: 94884d, 1978, p. 382 "Porous Powder Base for Cosmetics" JP 78 13626.
Chemical Abstracts, vol. 97, 150585m, 1982 "Porous Powder for Skin Cosmetics", JP 8281823.
JP-A-60-231607 (Kokai).
JP-A-61-194013 (Kokai).
J. Soc. Cosmet. Chem., 34 193 (1982).

*Primary Examiner*—Paul R. Michl
*Assistant Examiner*—Leon R. Horne
*Attorney, Agent, or Firm*—Sprung Horn Kramer & Woods

[57] ABSTRACT

A magnesium aluminometasilicate coated composite powder which comprises magnesium aluminometasilicate, or magnesium aluminometasilicate and at least one other powder coated on a surface of a core powder and which is usable in, for example, a skin treatment agent, deodorant, and oral composition.

13 Claims, 1 Drawing Sheet

Fig. 1

MAGNESIUM ALUMINOMETASILICATE COATED COMPOSITE POWDER AND USE THEREOF

CROSS-REFERENCE TO RELATED APPLICATION

This application is a continuation-in-part of Ser. No. 357,616, filed May 24, 1989, now abandoned, which is a continuation of Ser. No. 939,379 filed Dec. 8, 1986, now abandoned.

BACKGROUND OF THE INVENTION

1. Field of the Invention

The present invention relates to a magnesium aluminometasilicate coated composite powder wherein the surface of a core powder is substantially completely covered with a magnesium aluminometasilicate coating powder, thereby improving the surface characteristics, especially adsorpability, of the powder. More specifically, it relates to a magnesium aluminometasilicate coated composite powder and a skin treatment or external dermatological agent, deodorant, and oral composition using same, primarily to improve the adsorption property thereof.

Note that in this specification, "substantially completely covered" means a state wherein the core powder is homogeneously and closely covered by the coating powder. However, when microscopically examining the composite powder formed by substantially completely covering the core powder with the coating powder, it will be seen that there are extremely narrow gaps between the particles of the coating powder.

2. Description of the Related Art

Magnesium aluminometasilicate has the ability to adsorb skin wastes such as lower fatty acids and lipid peroxide, the ability to adsorbing unpleasant odor components, water adsorption and dissipation characteristics, and the action of solidifying skin fat components, and the like.

In the prior art, substances having various adsorption effects have been formulated in skin treatment agents, deodorants, and oral compositions, to achieve deodorization and the adsorption of skin wastes, and the like.

Accordingly, magnesium aluminometasilicate may be sometimes formulated in skin treatment agents, but there is no example of the use of magnesium aluminometasilicate in deodorants or oral compositions.

Fine particles of magnesium aluminometasilicate are liable to agglomeration, whereby various characteristics based on the adsorption ability thereof described above are not easily exhibited.

On the other hand, if the particles of magnesium aluminometasilicate are made larger, the agglomeration thereof can be inhibited, but a problem arises in that the various characteristics described above are considerably affected by the reduction of the surface area.

Accordingly, agglomeration occurs when magnesium aluminometasilicate is used as the powder component in a skin treatment agent, and further the dispersion stability is lost due to a high specific gravity thereof, whereby the cosmetic retentivity, skin waste adsorption ability, water adsorption and dissipation characteristic, and deodorizing effect possessed by magnesium aluminometasilicate is not easily exhibited, and the extendability thereof over the skin is heavy. Namely, the characteristics cannot be fully exhibited.

On the other hand, even if magnesium aluminometasilicate is used as the deodorizing component in a deodorant, due to its fine powdery form agglomeration occurs, and further, the specific surface area is reduced by this agglomeration to cause difficulty in exhibiting the deodorizing effect, and it is difficult to exhibit the required characteristics to their full extent.

Also, when magnesium aluminometasilicate is used as the powder component in an oral composition, agglomeration also occurs and the dispersion stability of the composition is lost due to the high specific gravity thereof, whereby the abrasive force and deodorizing effect of magnesium aluminometasilicate is exhibited only with difficulty, and further, the composition gives a feeling of roughness during use, and thus, the characteristics cannot be fully exhibited.

SUMMARY OF THE INVENTION

Accordingly, the objects of the present invention are to eliminate the above-mentioned disadvantages of the prior art and to provide a coated composite powder of magnesium aluminometasilicate having excellent powder characteristics such as an excellent adsorption without agglomeration and loss of dispersion stability, and a skin treatment agent, deodorant, and oral composition which fully exhibit the various characteristics of magnesium aluminometasilicate when included therein.

Other objects and advantages of the present invention will be apparent from the following description.

In accordance with the present invention, there is provided a magnesium aluminometasilicate coated composite powder which comprises magnesium aluminometasilicate, or magnesium aluminometasilicate and at least one other powder coated on a surface of a core powder.

In accordance with the present invention, there is also provided a skin treatment agent containing the above-mentioned magnesium aluminometasilicate coated composite powder.

In accordance with the present invention, there is further provided a deodorant containing the above-mentioned magnesium aluminometasilicate coated composite powder.

In accordance with the present invention, there is still further provided an oral hygiene product containing the above-mentioned magnesium aluminometasilicate coated composite powder.

BRIEF DESCRIPTION OF THE DRAWINGS

The present invention will be better understood from the description set forth below with reference to the accompanying FIG. 1, which is an electron microscope photograph (x 6000) showing the particulate structure of the magnesium aluminometasilicate coated composite powder obtained in Example 1 of the present invention.

DESCRIPTION OF THE PREFERRED EMBODIMENTS

As mentioned above, according to the present invention, the powder characteristics, typically the adsorption effect, can be improved to a great extent by coating the surface of a core powder with magnesium aluminometasilicate or magnesium aluminometasilicate and one or two or more kinds of other powders.

The constitution of the present invention is described in detail as follows.

Magnesium aluminometasilicate coated powder

As the core powder constituting the magnesium aluminometasilicate coated composite powder of the present invention, any desired organic or inorganic powder with an average particle size of 0.1 to 500 $\mu$m can be used, and the form of core powder may be any of a spheroid, plate, granule, or needle.

Examples of such a core powder include organic powders of polyamide resin, polyolefin resin, polystyrene, polyester resin, acrylic resin, epoxy resin, vinyl resin, vinylidene resin, polyurethane resin, natural rubber, synthetic rubber, chitin, chitosan, fibroin, keratin, cellulose, etc., and inorganic powders of talc, kaolin, mica, titanium dioxide, zinc white, zirconium oxide, anhydrous silicic acid, barium sulfate, iron oxide, mica, aluminium hydroxide chloride, calcium phosphate, and calcium secondary phosphate.

The magnesium aluminometasilicate preferably has an average particle size of 1/5 or less, more preferably 1/10 or less of the core powder.

If the average particle size of the magnesium aluminometasilicate is larger than 1/5 of the core powder, the elimination stability of the magnesium aluminometasilicate will be undesirably worsened.

On the other hand, as other powders to be coated together with the magnesium aluminometasilicate, various organic powders and inorganic powders can be used, but the average particle size thereof is preferably 1/5 or less, more preferably 1/10 or less, of the core powder, as in the case of the magnesium aluminometasilicate.

Also, the amounts to be formulated must be such that the effect of the magnesium aluminometasilicate is not impaired. Preferably, they are used at a ½ or less in terms of weight ratio to the magnesium aluminometasilicate used for coating.

Examples of such other powders include organic powders of polyamide resin, polyolefin resin, polystyrene, polyester resin, acrylic resin, epoxy resin, fluorine type resin, silicone type resin, phenol resin, vinyl resin, vinylidene resin, polyurethane resin, natural rubber, synthetic rubber, chitin, chitosan, fibroin, keratin, and cellulose, and inorganic powders of talc, kaolin, mica, titanium dioxide, zinc white, zirconium oxide, anhydrous silicic acid, barium sulfate, iron oxide, mica, aluminium hydroxide chloride, calcium phosphate, and calcium secondary phosphate.

The magnesium aluminometasilicate coated composite powder according to the present invention can be prepared by, for example, mixing magnesium aluminometasilicate (or magnesium aluminometasilicate and one or two or more kinds of other powders) with an organic core powder (or inorganic powder) by a dry process or wet process. As the mixing device, devices such as a ball mill, pot mill, mortar, automated mortar, attritor, mechanofusion system, and hybridization system may be employed.

The quantitative ratio when mixing magnesium aluminometasilicate (or magnesium aluminometasilicate and one or two or more kinds of other powders) and the organic core powder (or inorganic powder) is preferably 0.1 to 200 parts of magnesium aluminometasilicate (or magnesium aluminometasilicate and one or two or more kinds of other powders), more preferably 1 to 200 parts based on 100 parts of the organic powder, in terms of weight ratio. At less than 0.1 part, a magnesium aluminometasilicate coated powder having the required adsorption effect cannot be obtained.

Also, in this case, there is no change in the effect regardless of whether the surface of the core powder is completely coated with magnesium aluminometasilicate or magnesium aluminometasilicate and one or two or more kinds of other powders, or sparsely coated therewith.

Skin Treatment Agent Containing Magnesium Aluminometasilicate Coated Composite Powder The present invention is a skin treatment agent having a skin waste adsorption ability, deodorizing effect, and water adsorption and dissipation characteristic, and provides a good feeling during use.

The skin treatment agent mentioned above refers to basic cosmetics such as a cosmetic water, cream, emulsion, pack, and cosmetic base; washing agents such as a washing cream, cleansing cream, and soap; make-up cosmetics such as foundation, face powder, lipstick, rouge, eye liner, mascara, eye shadow, eyebrow pencil, and manicure; external deodorants such as deodorants or sweat controllers (aerosol, roll-on, powder, pressed powder, cream, stick), and the uses thereof include cosmetics, quasidrugs, and pharmaceuticals.

Particularly, an extremely good cosmetic retentivity can be obtained when used for make-up cosmetics.

The magnesium aluminometasilicate coated composite powder used in the present invention has particle sizes of 0.01 to 500 $\mu$m. Any desired shape can be used, but when a smooth feeling during use on the skin is required, a coated powder having a spheroid or plate shape is preferred, and in this case, the particle size is preferably 0.1 to 50 $\mu$m.

The amount of the above-mentioned coated powder in a skin treatment agent is preferably 0.1 to 100% by weight. At less than 0.1% by weight, the skin waste adsorption ability, water adsorption and dissipation characteristic, deodorizing effect, and cosmetic retentivity cannot be fully exhibited.

In the skin treatment agent of the present invention, in addition to the magnesium aluminometasilicate coated composite powder, general purpose components used in cosmetics, pharmaceuticals, and quasidrugs can be formulated. Examples of such components include oils and fats such as avocado oil, almond oil, olive oil, grape seed oil, sesame oil, sazanka oil, safflower oil, soy bean oil, tsubaki oil, corn oil, rapeseed oil, parsic oil, castor oil, sunflower oil, cottonseed oil, peanut oil, cacao oil, palm oil, coconut oil, tallow, fish fat, hardened oil, turtle oil, pig oil, mink oil, and yolk oil; waxes such as whale wax, shellac, beeswax, lanolin, liquid lanolin, carunauba wax, and candelilla wax; hydrocarbons such as fluid paraffin, fluid polyisobutylene, squalane, pristan, petrolatum, paraffin, and ceresin; fatty acids such as succinic acid, tartaric acid, citric acid, undecylenic acid, lauric acid, myristic acid, palmitic acid, stearic acid, isostearic acid, oleic acid, linoleic acid, ricinoleic acid, and behenic acid; alcohols such as ethanol, isopropanol, lauryl alcohol, cetanol, 2-hexyldecanol, stearyl alcohol, isostearyl alcohol, oleyl alcohol, and lanolin alcohol; polyhydric alcohols such as ethylene glycol, diethylene glycol monoethyl ether, triethylene glycol, polyethylene glycol, propylene glycol, 1,3-butylene glycol, glycerine, and butyl alcohol; sugars such as glucose, sucrose, lactose, xylitol, sorbitol, mannitol, and multitol; esters such as diisopropyl adipate, hexyldecyl isostearate, cetyl isooctanoate, oleyl oleate, decyl oleate, lanolin acetate, butyl stearate, isopropyl myristate, diethyl phthalate, and hexyl laurate; metal soaps such as aluminium stearate, magnesium stearate, and zinc stearate; natural water-soluble polymeric compounds such as gum arabic, sodium alginate, casein, carageenan, karaya gum, agar, quince seed, gelatin, dextrin, starch, tragacanth, and pectin; inorganic powder such as talc, kaolin, cericite, white mica, gold mica, red mica, black mica, litia mica, synthetic fluorine gold mica, vermicullite, magnesium carbonate, calcium carbonate, diatomaceous earth, magnesium silicate, calcium silicate, aluminium silicate, barium silicate, barium sulfate, strontium silicate, tungstic acid metal salt, silica, hydroxyapatite, zeolite, boron nitride, and ceramic powder; organic powder such as nylon powder, polyethylene powder, polystyrene powder, benzoguanamine powder, polytetrafluoroethylene powder, distyrenebenzene polymer powder, epoxy powder, acrylic powder, and microcrystalline cellulose; inorganic white powder such as titanium oxide and zinc oxide; inorganic red pigments such as iron oxide (blood red) and iron titanate; inorganic brown pigments such as $\gamma$-iron oxide; inorganic yellow pigments such as yellow iron oxide and yellow earth; inorganic black pigments such as black iron oxide and carbon black; inorganic violet pigments such as mango violet and cobalt violet; inorganic green pigments such as chromium oxide, chromium hydroxide, and cobalt titanate; inorganic blue pigments such as ultramarine and Prussian blue; pearl pigments such as titanium oxide coated mica, titanium oxide coated bismuth oxychloride, bismuth oxychloride, titanium oxide coated talc, fish scale, and colored titanium oxide coated mica; metal powder pigments such as aluminium powder and copper powder; organic pigments such as red color No. 201, red color No. 202, red color No. 204, red color No. 205, red color No. 220, red color No. 226, red color No. 228, red color No. 405, orange color No. 203, orange color No. 204, yellow color No. 205, yellow color No. 401, and blue color No. 404; organic pigments such as zirconium, barium or aluminium lake, etc., of red color No. 3, red color No. 104, red color No. 106, red color No. 227, red color No. 230, red color No. 401, red color No. 505, orange color No. 205, yellow color No. 4, yellow color No. 5, yellow color No. 202, yellow color No. 203, green color No. 3, and blue color No. 1; natural dyes such as chlorophyll and $\beta$-carotene; surfactants such as dialkylsulfosuccinates, alkylallylsulfonate, higher alcohol sulfate salts, and phosphoric acid ester salts; preservatives such as butyl paraoxybenzoate, propyl paraoxybenzoate, ethyl paraoxybenzoate, and methyl paraoxybenzoate; vitamins such as vitamin A, vitamin D, vitamin E, and vitamin K; hormones such as estradiol, ethynyl estradiol, and cortisone; sweat controllers such as aluminium hydroxychloride, aluminium chloride, aluminium sulfate, basic aluminium bromide, aluminium phenol sulfonic acid, tannic acid, aluminium naphthalene sulfonic acid, and basic aluminium iodide; sterilizers such as 3,4,4-trichlorocarbanylide (TCC), benzalconium chloride, benzetonium chloride, alkyltrimethyl ammonium chloride, resorcin, phenol, sorbic acid, salicyclic acid, and hexachlorophene; UV-ray absorbers such as urocanic acid and sinoxate; antiphlogistics such as alantoin, aloe powder, and guaizrene; propellants such as Freon 11, Freon 12, Freon 21, Freon 22, Freon 113, Freon 114, Freon C 318, methyl chloride, methylene chloride, isobutane, dimethyl ether, LPG (liquefied petroleum gas), and carbon dioxide; oil components such as silicone oil; surfactants; humectants; perfumes; water; alcohol; and thickeners.

Deodorant Containing Magnesium Aluminometasilicate Coated Composite Powder

The present invention is a deodorant having a good deodorizing effect.

The deodorant as mentioned above refers to, for example, a deodorant for a refrigerator, deodorant for a garbage can, in-room deodorant, deodorant for an automobile, leather insole for shoes, paper diaper, and a mensural product.

The magnesium aluminometasilicate coated composite powder to be used in the present invention has particle sizes of 0.01 to 500 $\mu$m, but preferably has particle sizes of 0.01 to 100 $\mu$m to ensure that the deodorizing effect is fully exhibited.

The amount of the above-mentioned coated composite powder formulated in the deodorant is preferably 0.1 to 100% by weight. At less than 0.1% by weight, the deodorizing effect cannot be fully exhibited.

In the deodorant of the present invention, in addition to the magnesium aluminometasilicate coated composite powder, various components generally used in deodorants can be formulated.

Examples of such components include oils and fats such as avocado oil, almond oil, olive oil, grape seed oil, sesami oil; sazanka oil, safflower oil, soy bean oil, tsubaki oil, corn oil, rapeseed oil, parsic oil, castor oil, sunflower oil, cottonseed oil, peanut oil, cacao oil, palm oil, coconut oil, tallow, fish fat, hardened oil, turtle oil, pig oil, mink oil, and yolk oil; waxes such as whale wax, shellac, beeswax, lanolin, liquid lanolin, carunauba wax, and candelilla wax; hydrocarbons such as fluid paraffin, fluid polyisobutylene, squalane, pristan, petrolatum, paraffin, and ceresin; fatty acids such as succinic acid, tartaric acid, citric acid, undecylenic acid, lauric acid, myristic acid, palmitic acid, stearic acid, isostearic acid, oleic acid, linoleic acid, ricinoleic acid, and behenic acid; alcohols such as ethanol, isopropanol, lauryl alcohol, cetanol, 2-hexyldecanol, stearyl alcohol isostearyl alcohol, oleyl alcohol, and lanolin alcohol; polyhydric alcohols such as ethylene glycol, diethylene glycol monoethyl ether, triethylene glycol, polyethylene glycol, propylene glycol, 1,3-butylene glycol, glycerine, and butyl alcohol; sugars such as glucose, sucrose, lactose, xylitol, sorbitol, mannitol, and multitol; esters such as diisopropyl adipate, hexyldecyl isostearate, cetyl isooctanoate, oleyl oleate, decyl oleate, lanolin acetate, butyl stearate, isopropyl myristate, diethyl phthalate, and hexyl laurate; metal soaps such as aluminium stearate, magnesium stearate, and zinc stearate; natural water-soluble polymeric compounds such as gum arabic, sodium alginate, casein, carageenan, karaya gum, agar, quince seed, gelatin, dextrin, starch, tragacanth, and pectin; inorganic powder such as talc, kaolin, cericite, white mica, gold mica, red mica, black mica, litia mica, synthetic fluorine gold mica, vermicullite, magnesium carbonate, calcium carbonate, diatomaceous earth, magnesium silicate, calcium silicate, aluminium silicate barium silicate, barium sulfate strontium silicate, tungstic acid metal salt, silica, hydroxyapatite, zeolite, boron nitride, and ceramic powder; organic powder such as nylon powder, polyethylene powder, polystyrene powder, benzoguanamine powder, polytetrafluoroethylene powder, distyrenebenzene polymer powder, epoxy powder, acrylic powder, and microcrystalline cellulose; inorganic white powder such as titanium oxide and zinc oxide; inorganic red pigments such as iron oxide (blood red) and iron titanate; inorganic brown pigments such as γ-iron oxide; inorganic yellow pigments such as yellow iron oxide and yellow earth; inorganic black pigments such as black iron oxide and carbon black; inorganic violet pigments such as mango violet and cobalt violet; inorganic green pigments such as chromium oxide, chromium hydroxide, and cobalt titanate; inorganic blue pigments such as ultramarine and Prussian blue; pearl pigments such as titanium oxide coated mica, titanium oxide coated bismuth oxychloride, bismuth oxychloride, titanium oxide coated talc, fish scale, and colored titanium oxide coated mica; metal powder pigments such as aluminium powder and copper powder; organic pigments such as red color No. 201, red color No. 202, red color No. 204, red color No. 205, red color No. 220, red color No. 226, red color No. 228, red color No. 405, orange color No. 203, orange color No. 204, yellow color No. 205, yellow color No. 401, and blue color No. 404; organic pigments such as zirconium, barium or aluminium lake, etc. of red color No. 3, red color No. 104, red color No. 106, red color No. 227, red color No. 230, red color No. 401, red color No. 505, orange color No. 205, yellow color No. 4, yellow color No. 5, yellow color No. 202, yellow color No. 203, green color No. 3, and blue color No. 1; natural dyes such as chlorophyll and ⊕-carotene; surfactants such as dialkylsulfosuccinates, alkylallylsulfonate, higher alcohol sulfate salts, and phosphoric acid ester salts; preservatives such as butyl paraoxybenzoate, propyl paraoxybenzoate, ethyl paraoxybenzoate, and methyl paraoxybenzoate; vitamins such as vitamin A, vitamin D, vitamin E, and vitamin K; hormones such as estradiol, ethynyl estradiol, and cortisone; sweat controllers such as aluminium hydroxychloride, aluminium chloride, aluminium sulfate, basic aluminium bromide, aluminium phenol sulfonic acid, tannic acid aluminium naphthalene sulfonic acid, and basic aluminium iodide; sterilizers such as 3,4,4-trichlorocarbanylide (TCC), benzalconium chloride, benzetonium chloride, alkyltrimethyl ammonium chloride, resorcin, phenol, sorbic acid, salicylic acid, and hexachlorophene; UV-ray absorbers such as urocanic acid and sinoxate; antiphlogistics such as alantoin, aloe powder, and guaizrene; propellants such as Freon 11, Freon 12, Freon 21, Freon 22, Freon 113, Freon 114, Freon C 318, methyl chloride, methylene chloride, isobutane, dimethyl ether, LPG (liquefied petroleum gas), and carbon dioxide; oil components such as silicone oil; surfactants; humectants; perfumes; water; alcohol; and thickeners.

Oral Hygiene Product containing Magnesium Aluminometasilicate Coated Composite Powder The present invention is an oral hygiene product having a good dispersion stability, abrasive force, and deodorizing effect.

The oral hygiene product as mentioned above refers to, for example, a toothpaste, mouthwash, and deodorizing liquid, and the like.

The magnesium aluminometasilicate coated composite powder to be used in the present invention has particle sizes of 0.01 to 500 μm. Any desired shape can be used, but when a smooth feeling of use in the mouth is required, a coated powder having a spheroid or plate shape is preferred, and the particle sizes in this case are preferably 0.1 to 50 μm.

The amount of the above-mentioned coated powder in an oral hygiene product is preferably 0.1 to 100% by weight. At less than 0.1% by weight, the abrasive force or the deodorizing effect cannot be fully exhibited.

In the oral hygiene product of the present invention, in addition to the above-mentioned coated composite powder, various components generally used in oral compositions can be formulated.

For example, there can be formulated abrasives such as calcium carbonate, calcium phosphate, calcium secondary phosphate, anhydrous silicic acid, hydrous silicic acid, calcium pyrophosphate, insoluble sodium metaphosphate, and alumina; thickeners such as carboxymethylcellulose, methyl cellulose, hydroxyethyl cellulose, carageenan, sodium alginate, beegum, bentonite, and polyvinyl alcohol; wetting agents such as glycerine, sorbitol, propylene glycol, and polyethylene glycol; foaming agents such as sodium lauryl sulfate, sodium acyl sarcosinate, sucrose fatty acid ester, and sodium fatty acid monoglyceride monosulfate; sweeteners such as saccharin sodium, stebioside, glycyrrhitin, and somatin; preservatives; perfumes; fluorine compounds; drugs such as antibacterial agents and antiinflammatory agents; and colorants, if required.

EXAMPLES

The present invention will now be further illustrated by, but is by no means limited to, the following examples, wherein all parts and percentages are expressed on a weight basis unless otherwise noted.

Preparation of Magnasium Aluminometasilicate Coated Composite Powder

First, Examples of magnesium aluminometasilicate coated composite powder will be described.

The magnesium aluminometasilicate used in the following Examples is primarily Neucilin FH1, FH2, FL1, FL2, NFL2N, and UFL2 manufactured by Fuji Kagaku Kogyo K.K., but the invention is not limited thereto.

Example 1: Magnesium Aluminometasilicate (25.0%) Coated Spherical Nylon 12

First, 75.0% of spherical nylon 12 (average particle size 6.6 μm) was mixed with 25.0% of magnesium aluminometasilicate (average particle size 0.3 μm) in a Henschel type mixer (FM10B model, Mitsui Miike Seisakusho) for 3 minutes, and then the mixed powder was treated in a rotatory system ball mill (Yamato Kagaku, Universal Ball Mill) filled with alumina balls (Nippon Kagaku Togyo, HD Alumina Ball 3 mmφ) for 10 hours.

Figure 1:
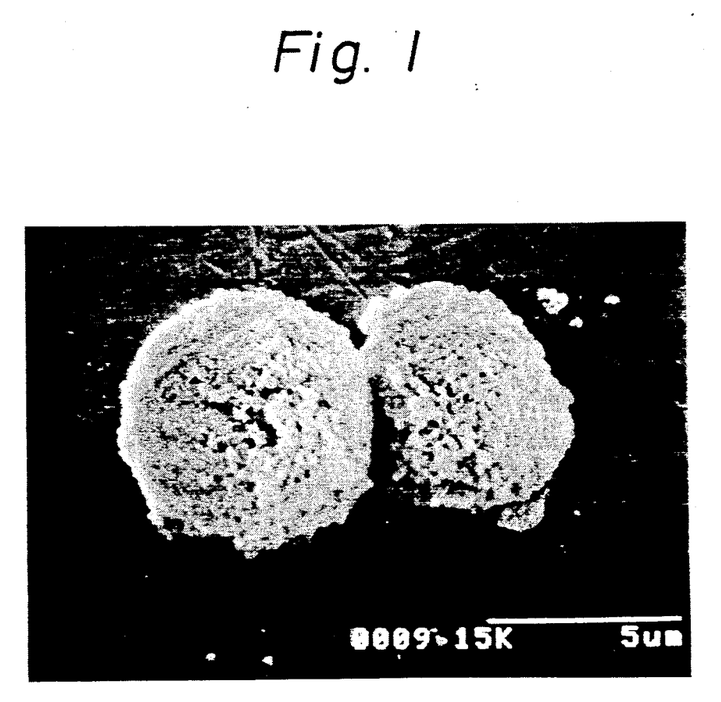

Observation by a scanning electron microscope (scanning electron microscope, S-510 model, produced by Hitachi) confirmed that the coated powder having the particulate structure shown in FIG. 1 was obtained.

The scale at the right lower side of the same figure indicates 5 μm.

Example 2: Magnesium Aluminometasilicate (20.0%) Coated Plate-Shaped Polyethylene First, 80.0% of plate-shaped polyethylene (average particle size 10 μm) was mixed with 20.0% of magnesium aluminometasilicate (average particle size 0.03 μm) in a small scale pulverizer (Kyoritsu Riko, SK-M10 model) for 1 minute, and then the mixed powder was placed in a planetary ball mill (Centrifugal Ball Mill, manufactured by Mitamura Riken Kogyo) filled with alumina balls (Nippon Kagaku Togyo, HD Alumina Ball 2 mmφ), and the treatment was carried out for 1 hour. It was confirmed by scanning electron microscope observation that, in the coated powder, the surface of the plate-shaped polyethylene was completely covered with magnesium aluminometasilicate.

Example 3: Magnesium Aluminometasilicate (15%) And Silicon Dioxide (15%) Coated Granular Cellulose First, 70.0% of granular cellulose (average particle size 20 μm) was treated with 15.0% of magnesium aluminometasilicate (average particle size 0.3 μm) and 15.0% of silicon dioxide (average particle size 0.1 μm) in a rotatory system ball mill (Universal Ball Mill manufactured by Yamato Kagaku) filled with alumina balls (HD Alumina Ball 3 mmφ manufactured by Nippon Kagaku Togyo), for 8 hours to obtain a coated powder.

Example 4: Magnesium Aluminometasilicate (39.0%) Coated Spherical Polystyrene

First, 61.0% of spherical polystyrene powder (average particle size 50 μm) was placed with 39.0% of magnesium metasilicate aluminate (average particle size 2 μm) in a planetary ball mill (Mitamura Riken Kogyo, CENTRIFUGAL BALL MILL) filled with alumina balls (Ashizawa Alumina Ball 1 mmφ), and the treatment was carried out for 30 minutes to obtain a coated powder.

Example 5: Magnesium Aluminometasilicate (18.0%) And Zinc Oxide (10.0%) Coated Spherical Polymethyl Methacrylate First, 72.0% of spherical polymethyl methacrylate (average particle size 0.5 μm) was placed with 18.0% of magnesium aluminometasilicate (average particle size 0.03 μm) and 10.0% of zinc oxide (average particle size 0 03 μm) in a vibration system ball mill (Nippon Spindle, VKM-2 model) filled with alumina balls (Ashizawa Alumina Ball 2 mmφ), and the treatment was carried out for 3 hours to obtain a coated powder.

Example 6: Magnesium Aluminometasilicate (20.0%) Coated Spherical Polyethylene

First, 80.0% of spherical polyethylene powder (average particle size 5 μm) and 20.0% of magnesium aluminometasilicate (average particle size 0.5 μm) were subjected to the OM Dizer treatment for 1 minute and the hybridizer treatment (3000 rpm) for 2 minutes, using a hybridization system (NHS-1 model manufactured by Nara Kikai), to obtain a coated powder.

Example 7: Magnesium Aluminometasilicate (20.0%) Coated Spherical Silicon Dioxide First, 80.0% of spherical silicon dioxide (average particle size 7 μm) and 20.0% of magnesium aluminometasilicate (average particle size 0.05 μm) were thrown into the rotatory casing section of a mechanofusion system (AM-15F model manufactured by Hosokawa Micron), and the treatment was carried out at 2800 rpm for 30 minutes to obtain a coated powder.

Example 8: Magnesium Aluminometasilicate (7.0%) And Red Iron Oxide (3.0%) Coated Spherical Chitosan First, 90.0% of spherical chitosan powder (average particle size 3 μm) together with 7.0% of magnesium aluminometasilicate (average particle size 0.2 μm) and 3.0% of red iron oxide (average particle size 0.3 μm) were placed into a jet mill (Micron Jet MJ-3 model manufactured by Hosokawa Micron) modified to non-continuous system, and the treatment was carried out for 30 minutes to obtain a coated powder.

Example 9: Magnesium Aluminometasilicate (25.0%) And Titanium Dioxide (8.0%) Coated Spherical Dimethyl Polysiloxane Powder First, 67.0% of spherical dimethyl polysiloxane powder (average particle size 9 μm) together with 25.0% of magnesium aluminometasilicate and 8.0% of titanium dioxide were placed in a Cosmomizer (COS-1 model manufactured by Nara Kikai) modified to a continuous system, and the treatment was carried out at 3000 rpm for 10 minutes to obtain a coated powder.

Example 10: Magnesium Aluminometasilicate (15.0%) Coated Plate-Shaped Boron Nitride First, 85.0% of plate-shaped boron nitride (average particle size 8 μm) together with 15.0% of magnesium aluminometasilicate (average particle size 0.1 μm) were subjected to the OM Dizer treatment for 2 minutes and the hybridizer treatment (2600 rpm) for 3 minutes, by using a hybridization system (MHS-2 model manufactured by Nara Kikai) to obtain a coated powder.

Example 11: Magnesium Aluminometasilicate (12.0%) Coated Wool Keratin Powder

First, 88.0% of wool keratin powder (average particle size 20 μm) together with 12.0% of magnesium metasilicate aluminate (average particle size 0.02 ∞m) and half the amount of the powder amount of ethanol were placed in a rotatory system ball mill (V-2M model manufactured by Irie Shokai) filled with zirconia balls of 5 mmφ, and the treatment was carried out for 6 hours to obtain a coated powder.

Example 12: Magnesium Aluminometasilicate (15.0%) And Hydroxyapatite (5.0%) Coated Particulate Polytetrafluoroethylene Using 80.0% of particulate polytetrafluoroethylene (average particle size 5 μm), 15.0% of magnesium metasilicate aluminate (average particle size 0.01 μm), and 5.0% of hydroxyapatite (average particle size 0.1 μ), a coated powder was obtained by the same method as in Example 1.

Example 13: Magnesium Aluminometasilicate (25.0%) And Zinc Oxide (15.0%) Coated Spherical Crosslinked Dimethyl Polysiloxane Using 60.0% of spherical crosslinked dimethyl polysiloxane (average particle size 3 μm), 25.0% of magnesium aluminometasilicate (0.03 μm), and 15.0% of zinc dioxide (0.05 μm), a coated powder was obtained by the same method as in Example 2.

Example 14: Magnesium Aluminometasilicate (15.0%) And Spherical polyMMA (5.0%) Coated Particulate Starch Using 80.0% of particulate starch (average particle size 30 μm), 15.0% of magnesium aluminometasilicate (average particle size 0.5 μm), and 5.0% of spherical polyMMA (average particle size 0.3 μm), a coated powder was obtained according to the same method as in Example 3.

Example 15: Magnesium Aluminometasilicate (25.0%) And Barium Sulfate (10.0%) Coated Spherical Cured Bisphenol A-Epichlorohydrin Copolymer Powder Using 65.0% of spherical cured bisphenol A-epichlorohydrin copolymer powder (average particle size 3 μm), 25.0% of magnesium aluminometasilicate (average particle size 0.05 μm), and 10.0% of barium sulfate (average particle size 0.5 μm), a coated powder was obtained by the same method as in Example 3.

Example 16: Magnesium Aluminometasilicate (15.0%) Coated Plate-Shaped Polyethylene Using 85.0% of plate-shaped polyethylene (average particle size 8 μm) and 15.0% of magnesium aluminometasilicate (average particle size 0.2 μm), a coated powder was obtained by the same method as in Example 1.

Example 17: Magnesium Aluminometasilicate (28.0%) Coated Spherical Nylon 6

Using 72.0% of spherical nylon 6 (average particle size 9 μm) and 28.0% of magnesium aluminometasilicate (average particle size 0.04 μm), a coated powder was obtained by the same method as in Example 2.

Example 18: Magnesium Aluminometasilicate (40.0%) Coated Fibrous Cellulose Powder Using 60.0% of fibrous cellulose powder (average particle size 10 μm) and 40.0% of magnesium aluminometasilicate (average particle size 0.05 μm), a coated powder was obtained by the same method as in Example 11.

Example 19: Magnesium Aluminometasilicate (35.0%) Coated Spherical Benzoguanamine Resin Using 65.0% of spherical benzoguanamine resin (average particle size 30 μm) and 35.0% of magnesium aluminometasilicate (average particle size 1.0 μm), a coated powder was obtained by the same method as in Example 4.

Example 20: Magnesium Aluminometasilicate (20.0%) And Zinc Oxide (10.0%) Coated Plate-Shaped Silicon Dioxide Using 70% of plate-shaped silicon dioxide (average particle size 12 μm), 20.0% of magnesium aluminometasilicate (average particle size 0.05 μm), and 10.0% of zinc oxide (average particle size 0.2 μm), a coated powder was obtained by the same method as in Example 5.

Example 21: Magnesium Aluminometasilicate (25.0%) Coated Particulate Chitin

Using 75.0% of particulate chitin (average particle size 50 μm) and 25.0% of magnesium aluminometasilicate (average particle size 5 μm), a coated powder was obtained by the same method as in Example 6.

Example 22: Magnesium Aluminometasilicate (15.0%) And Polytetrafluoroethylene (5.0%) Coated Silk Fibroin Powder Using 80.0% of silk fibroin powder (average particle size 25 μm), 15.0% of magnesium aluminometasilicate (average particle size 0.2 μm), and 5.0% of polytetrafluoroethylene (average particle size 1 μm), a coated powder was obtained by the same method as in Example 7.

Example 23: Magnesium Aluminometasilicate (22.0%) Coated Spherical Chitosan

Using 78.0% of spherical chitosan (average particle size 10 μm) and 22.0% of magnesium aluminometasilicate (average particle size 0.7 μm), a coated powder was obtained by the same method as in Example 8.

Example 24: Magnesium Aluminometasilicate (30.0%) And Hydroxyapatite (10.0%) Coated Particulate Silicon Dioxide Using 60.0% of particulate silicon dioxide (average particle size 20 μm), 30.0% of magnesium aluminometasilicate (average particle size 0.5 μm), and 10.0% of hydroxyapatite (average particle size 0.2 μm), a coated powder was obtained by the same method as in Example 9.

Example 25: Magnesium Aluminometasilicate (33.0%) Coated Particulate Cellulose

Using 67.0% of particulate cellulose (average particle size 35 μm) and 33.0% of magnesium aluminometasilicate (average particle size 0.05 μm), a coated powder was obtained by the same method as in Example 10.

Example 26: Magnesium Aluminometasilicate (20.0%) And Silicon Dioxide (20.0%) Coated Fibrous Nylon 12

Using 60.0% of fibrous nylon 12 (average particle size 45 μm), 20.0% of magnesium aluminometasilicate (average particle size 0.9 μm), and 20.0% of silicon dioxide (average particle size 1.0 μm), a coated powder was obtained by the same method as in Example 11.

Skin Treatment Agent Containing Magnesium Aluminometasilicate Coated Composite Powder Examples of external skin treatment agents containing the magnesium aluminometasilicate coated composite powder are described.

Example 27: Powder Foundation

|  | Parts |
|---|---|
| (1) Cericite | 47.28 |
| (2) Talc | 15.0 |
| (3) Magnesium aluminometasilicate (25%) coated spherical nylon 12 (product of Example 1) | 15.0 |
| (4) Titanium dioxide | 6.5 |
| (5) Iron oxide | 3.5 |
| (6) Trimethylolpropane triisostearate | 5.0 |
| (7) Squalane | 6.0 |
| (8) Sorbitan sesquioleate | 1.0 |
| (9) Preservative | 0.5 |
| (10) Antioxidant | 0.02 |
| (11) Perfume | 0.2 |

Preparation method

The above (1) to (5) were mixed in a Henschel mixer, and (6) to (11) were melted by heating and added thereto, followed by mixing and pulverization. The resultant mixture was molded into a medium size dish to obtain a powder foundation.

The following is a Comparative Example.

|  | Parts |
|---|---|
| (1) Cericite | 47.28 |
| (2) Talc | 15.0 |
| (3) Magnesium aluminometasilicate | 3.75 |

-continued

|  | Parts |
|---|---|
| (4) Spherical nylon 12 | 11.25 |
| (5) Titanium dioxide | 6.5 |
| (6) Iron oxide | 3.5 |
| (7) Trimethylolpropane triisostearate | 5.0 |
| (8) Squalane | 6.0 |
| (9) Sorbitan sesquioleate | 1.0 |
| (10) Preservative | 0.5 |
| (11) Antioxidant | 0.02 |
| (12) Perfume | 0.2 |

The preparation method was conducted according to Example 27.

Next, the effect was confirmed by a practical use test. The faces of 25 women testees having healthy skin were coated with the powder foundation obtained in Example 27 and the powder foundation comprising magnesium aluminometasilicate formulated as such, without coating the spherical nylon 12 as shown in Comparative Example, at desired sites on the right half and the left half on their faces, the testees remained in a thermostat and humidistat chamber (temperature 28° C., humidity 70%) for 2 hours, and the cosmetic retentivity effects examined.

The results are shown in Table 1.

As apparent from Table 1, many testees felt that Example 27 had a far better cosmetic retentivity than Comparative Example 1, thus suggesting that the coating of magnesium aluminometasilicate effectively improves the cosmetic retentivity.

TABLE 1

|  | Example 27 | Comparative Example |
|---|---|---|
| Very good | 16 testees | 2 testees |
| Good | 6 testees | 10 testees |
| Bad | 3 testees | 13 testees |

Example 28: Solid Powdery Skin Treatment Agent

|  | Parts |
|---|---|
| (1) Talc | 19.8 |
| (2) Magnesium stearate | 5.0 |
| (3) Magnesium aluminometasilicate (20%) coated plate-shaped polyethylene (product of Example 2) | 75.0 |
| (4) Perfume | 0.1 |
| (5) Sterilizer | 0.1 |

Preparation method

While the components (1) to (3) and (5) were thoroughly stirred and mixed in a blender, the component (4) was sprayed thereon, and the resultant mixture was molded into a medium size dish to obtain a solid powdery external dermatological agent.

The following is a Comparative Example.

|  | Parts |
|---|---|
| (1) Talc | 19.8 |
| (2) Magnesium stearate | 5.0 |
| (3) Magnesium aluminometasilicate | 15.0 |
| (4) Plate-shaped polyethylene | 60.0 |
| (5) Perfume | 0.1 |
| (6) Sterilizer | 0.1 |

The preparation method was conducted according to Example 28.

Next, the effect was confirmed by a practical use text.

The faces of 20 testees suffering from skin roughening were coated with the solid powdery external dermatological gent obtained in Example 28 and the powdery external dermatological agent not coated with magnesium aluminometasilicate, continuously over a period of 3 months, to determine the skin roughening reduction effect.

The results are shown in Table 2.

From Table 2 it is clear that 50% or more of the testees that Example 28 "clearly reduced skin roughening" and "slightly reduced skin roughening", compared with the Comparative Example, thus suggesting that the coating of magnesium aluminometasilicate obviates skin roughening.

TABLE 2

|  | Example 28 | Comparative Example |
|---|---|---|
| Clearly reduced | 9 testees | 2 testees |
| Slightly reduced | 8 testees | 9 testees |
| No effect | 3 testees | 9 testees |

Example 29: Powdery Skin Treatment Agent

|  | Parts |
|---|---|
| (1) Talc | 49.95 |
| (2) Magnesium aluminometasilicate (15%) and silicon dioxide (15%) coated particulate cellulose (product of Example 3) | 50.0 |
| (3) Perfume | 0.05 |

Preparation method

While (1) and (2) were thoroughly stirred and mixed by a blender, (3) was uniformly sprayed thereon to obtain a powdery external dermatological agent.

The following is a Comparative Example.

|  | Parts |
|---|---|
| (1) Talc | 49.95 |
| (2) Magnesium aluminometasilicate | 7.5 |
| (3) Silicon dioxide | 7.5 |
| (4) Particulate cellulose | 35.0 |
| (5) Perfume | 0.05 |

The preparation method was conducted according to Example 29.

Next, the effect was confirmed by a practical use test.

The faces of 10 testees suffering from pimples were coated with the powdery external dermatological agent obtained in Example 29 and the powdery external dermatological agent of Comparative Example not coated with magnesium aluminometasilicate and silicon dioxide, continuously for a period of 3 months, to determine the reduction of the inflammation induced by the pimples.

The test results are shown in Table 3.

From Table 3 it is clear that 80% or more of the testees felt that Example 29 "clearly reduced inflammation" and "slightly reduced inflammation", compared with the Comparative Example, thus suggesting that the coating with magnesium aluminometasilicate and silicon dioxide effectively reduced inflammation induced by pimples.

TABLE 3

| | Example 29 | Comparative Example |
|---|---|---|
| Clearly reduced | 7 testees | 2 testees |
| Slightly reduced | 2 testees | 3 testees |
| No effect | 1 testee | 5 testees |

Example 30: Cleansing Cream

| | | Parts |
|---|---|---|
| (1) | Cetanol | 2.0 |
| (2) | Beeswax | 2.0 |
| (3) | Stearic acid | 3.0 |
| (4) | Petrolatum | 8.0 |
| (5) | Squalane | 37.0 |
| (6) | Isopropyl myristate | 10.0 |
| (7) | P.O.P. (20 mol) sorbitan lauric acid ester | 2.5 |
| (8) | Glycerine monostearate | 2.5 |
| (9) | Ethyl parabene | 0.3 |
| (10) | Perfume | 0.2 |
| (11) | Glycerine | 2.0 |
| (12) | Propylene glycol | 5.0 |
| (13) | Purified water | 20.4 |
| (14) | Potassium hydroxide | 0.1 |
| (15) | Magnesium aluminometasilicate (39.0%) coated spherical polystyrene (product of Example 4) | 5.0 |

Preparation method

After (1) to (10) and (11) to (14) were respectively heated to 70° C. to be dissolved, the dissolved product of (1) to (10) was added to the dissolved product of (11) to (14), the mixture was emulsified by an emulsifier, the emulsion was cooled by a heat exchanger to a final temperature of 30° C., and then filled in a vessel.

The following is a Comparative Example.

| | | Parts |
|---|---|---|
| (1) | Cetanol | 2.0 |
| (2) | Beeswax | 2.0 |
| (3) | Stearic acid | 3.0 |
| (4) | Petrolatum | 8.0 |
| (5) | Squalane | 37.0 |
| (6) | Isopropyl myristate | 10.0 |
| (7) | P.O.P. (20 mol) sorbitan lauric acid ester | 2.5 |
| (8) | Glycerine monostearate | 2.5 |
| (9) | Ethyl parabene | 0.3 |
| (10) | Perfume | 0.2 |
| (11) | Glycerine | 2.0 |
| (12) | Propylene glycol | 5.0 |
| (13) | Purified water | 20.4 |
| (14) | Potassium hydroxide | 0.1 |
| (15) | Magnesium aluminometasilicate | 1.95 |
| (16) | Spherical polystyrene | 3.05 |

The preparation method was conducted according to Example 30.

Next, the effect was confirmed by a practical use test.

The faces of 20 women testees having healthy skin were coated with the cleansing cream obtained in Example 30 and the cleansing cream of the Comparative Example not coated with magnesium aluminometasilicate, on the left and right of the face, and the feeling during use was determined.

The test results are shown in Table 4.

From Table 4, it is clear that Example 30 has a better feeling during use than the Comparative Example, suggesting that the coating of magnesium aluminometasilicate is more effective for improving the feeling during use of the cleansing cream.

TABLE 4

| | Example 30 | Comparative Example |
|---|---|---|
| Very good | 16 testees | 1 testee |
| Good | 3 testees | 8 testees |
| Bad | 1 testee | 11 testees |

Example 31: Compact-Shaped Deodorant Powder

| | | Parts |
|---|---|---|
| (1) | Magnesium aluminometasilicate (18.0%) and zinc oxide (10.0%) coated spherical polymethyl methacrylate (product of Example 5) | 60.0 |
| (2) | Zinc myristate | 10.0 |
| (3) | Talc | 20.0 |
| (4) | Liquid paraffin | 10.0 |

Preparation method

The components (1) to (3) were mixed in a Henschel mixer, the component (4) was added to the mixture, the mixture was pulverized by a 5HP pulverizer (Hosokawa Micron), and the pulverized product was press molded into a medium size dish to obtain a compact-shaped deodorant powder according to the present invention.

The following is a Comparative Example.

| | | Parts |
|---|---|---|
| (1) | Magnesium aluminometasilicate | 10.8 |
| (2) | Zinc oxide | 6.0 |
| (3) | Spherical polymethyl methacrylate | 43.2 |
| (4) | Zinc myristate | 10.0 |
| (5) | Talc | 20.0 |
| (6) | Fluid paraffin | 10.0 |

The preparation method was conducted according to Example 31.

Next, the effect was confirmed by a practical use test.

The deodorant effect test of the compact-shaped deodorant powder of the present invention was conducted on 10 healthy men who were aware of having an axillary odor. The testees who bathed the night before were coated 15 hours later on one underarm with the powder obtained in Example 30 and on the other underarm by the powder of Comparative Example, at the same time, and each individual evaluated the odors from both underarms one minute later.

The test results are shown in Table 5.

From Table 5 it is clear that the deodorant effect of Example 31 is better than that of Comparative Example 1, suggesting that the coating of magnesium aluminometasilicate and zinc oxide provides a more effective improvement of the deodorant effect of the compact-shaped deodorant powder.

TABLE 5

| | Example 31 | Comparative Example |
|---|---|---|
| No smell | 5 testees | 0 testees |
| Very good deodorant effect | 4 testees | 1 testee |
| Good deodorant effect | 1 testee | 2 testees |
| Slight deodorant effect | 0 testees | 6 testees |

TABLE 5-continued

|  | Example 31 | Comparative Example |
|---|---|---|
| No deodorant effect | 0 testees | 1 testee |

Example 32: Deodorant Spray

|  |  | Parts |
|---|---|---|
| (1) | Freon 11 | 76.8 |
| (2) | Freon 12 | 19.2 |
| (3) | Magnesium aluminometasilicate (20%) coated spherical polyethylene (product of Example 6) | 3.0 |
| (4) | Isopropyl myristate | 0.5 |
| (5) | Tetra-2-ethylhexanoic acid diglycerol sorbitan | 0.5 |

Preparation method

After (3) to (5) were mixed by a kneader, the mixture was filled into a spray can, and then (1) and (2) were filled therein to obtain a deodorant spray.

The following is a Comparative Example.

|  |  | Parts |
|---|---|---|
| (1) | Freon 11 | 76.8 |
| (2) | Freon 12 | 19.2 |
| (3) | Magnesium aluminometasilicate | 0.6 |
| (4) | Polyethylene | 2.4 |
| (5) | Isopropyl myristate | 0.5 |
| (6) | Tetra-2-ethylhexanoic acid diglycerol sorbitan | 0.5 |

The preparation method was conducted according to Example 32.

Next, the effect was confirmed by a practical use test.

The deodorant effect test of the deodorant spray of the present invention was conducted on 20 healthy men aware of having foot odor. The testees who bathed the night before were coated 18 hours later on one bare foot with the deodorant spray obtained in Example 32, and on the other foot with the deodorant spray of the Comparative Example, at the same time, and each individual evaluated the odor of both feet one minute later.

The test results are shown in Table 6.

From Table 6, it is clear that Example 32 had a better deodorant effect than the Comparative Example, suggesting that the coating of magnesium aluminometasilicate provides a more effective improvement of the deodorant effect of the deodorant spray.

TABLE 6

|  | Example 32 | Comparative Example |
|---|---|---|
| No smell | 10 testees | 0 testees |
| Very good deodorant effect | 7 testees | 1 testee |
| Good deodorant effect | 3 testees | 9 testees |
| Slight deodorant effect | 0 testees | 10 testees |
| No deodorant effect | 0 testees | 1 testee |

Example 33: Ointment

|  |  | Parts |
|---|---|---|
| (1) | Ceresin | 20.0 |
| (2) | Liquid paraffin | 18.0 |
| (3) | P.O.E. (10 mol) monooleic acid ester |  0.25|
| (4) | Glycerine monostearic acid ester | 0.25 |
| (5) | Petrolatum | 35.0 |
| (6) | Magnesium aluminometasilicate (20.0%) coated spherical silicon dioxide (product of Example 7) | 5.0 |
| (7) | Purified water | 17.5 |
| (8) | Propylene glycol | 4.0 |

Preparation method

The components (1) to (5) were dissolved by mixing at 70° C. (oil phase), and (6) then dispersed therein. A solution of (8) dissolved in (7) was maintained at 70° C., and added to the oil phase, and the mixture was homogeneously emulsified by a homomixer, followed by cooling to obtain an ointment.

The ointment obtained in Example 33 was found to have an excellent effect of reducing skin roughening in practical use, compared with the ointment in which magnesium aluminometasilicate was used as such without coating.

|  |  | Parts |
|---|---|---|
| (1) | Polyvinyl alcohol | 15.0 |
| (2) | Polyethylene glycol | 3.0 |
| (3) | Propylene glycol | 7.0 |
| (4) | Ethanol | 10.0 |
| (5) | Magnesium aluminometasilicate (7%) and red iron oxide (3%) coated spherical chitosan (product of Example 8) | 10.0 |
| (6) | Methyl parabene | 0.05 |
| (7) | Perfume | 0.15 |
| (8) | Purified water | 54.8 |

Preparation method

First, (2), (3), and (6) were added to (8) and dissolved therein. Then (1) was added to be dissolved by heating under stirring, (5) was dispersed in the solution, and to the dispersion were added (4) and (7), followed by stirring and dissolving to obtain a pack.

As the result of a practical use test, the pack according to this Example was found to have a smooth feeling during use and an excellent effect of suppressing stickiness of the skin due to skin fat.

Example 35: Cream

|  |  | Parts |
|---|---|---|
| (1) | Cetostearyl alcohol | 3.5 |
| (2) | Squalane | 20.0 |
| (3) | Beeswax | 3.0 |
| (4) | Lanolin | 5.0 |
| (5) | Ethyl parabene | 0.3 |
| (6) | P.O.E. (20 mol) sorbitan monooleic acid ester | 2.0 |
| (7) | Stearic acid monoglyceride | 2.0 |
| (8) | Magnesium aluminometasilicate (25%) and titanium dioxide (8%) coated spherical dimethyl polysiloxane powder (product of Example 9) | 5.0 |
| (9) | Perfume | 0.1 |
| (10) | 1,3-butylene glycol | 5.0 |
| (11) | Glycerine | 5.0 |
| (12) | Purified water | 49.1 |

Preparation method

The components (1) to (7) and (9) were dissolved by heating an maintained at 75° C. (oil phase). Then, after (10) and (11) were dissolved in (12), (8) was added to be dispersed in the solution and heated to 75° C. (aqueous phase). The oil phase was then added to the aqueous phase and emulsified by the homomixer, followed by cooling to obtain a cream.

The cream according to this Example was found to have a good dispersion stability of the powder components and an excellent feeling during use.

Example 36: Compact Powder

|  | Parts |
|---|---|
| (1) Talc | 87.9 |
| (2) Magnesium aluminometasilicate (15%) coated plate-shaped boron nitride (product of Example 10) | 10.0 |
| (3) Liquid paraffin | 2.0 |
| (4) Perfume | 0.1 |

Preparation method

While (1) and (2) were stirred and mixed well by a blender, (3) and (4) were uniformly sprayed thereon and the mixture was molded into a medium size dish to obtain a compact powder.

The solid white powder according to this Example was found to have a smooth feeling during use and an excellent cosmetic retentivity.

Example 37: Baby Powder

|  | Parts |
|---|---|
| (1) Talc | 80.0 |
| (2) Calcium carbonate | 17.0 |
| (3) Starch | 0.5 |
| (4) Magnesium aluminometasilicate (12.0%) coated wool keratin powder (product of Example 11) | 2.0 |
| (5) Sterilizer | 0.3 |
| (6) Preservative | 0.2 |

Preparation method

The components (1) to (6) were thoroughly stirred and mixed by a blender to obtain a baby powder.

The baby powder according to this Example was found to have a smooth feeling during use, and an excellent body odor deodorizing effect and inhibition of the formation of prickly heat.

Example 38: Deodorant Stick

|  | Parts |
|---|---|
| (1) Octamethylcyclotetrasiloxane | 60.0 |
| (2) Squalane | 10.0 |
| (3) Hydrocarbon wax | 10.0 |
| (4) Magnesium aluminometasilicate (15%) and hydroxyapatite (5%) coated spherical polytetrafluoroethylene (product of Example 12) | 20.0 |

Preparation method

A mixture of the components (1) to (4) were mixed while heating, and filled in a vessel to obtain a deodorant stick.

The deodorant stick according to this Example, when coated on the underarm, was found to have a light feeling and an excellent deodorizing effect.

Example 39: Roll-On Deodorant

|  | Parts |
|---|---|
| (1) Purified water | 71.0 |
| (2) Ethanol | 20.0 |
| (3) Sorbitol | 4.0 |
| (4) Magnesium aluminometasilicate (25%) and zinc oxide (15%) coated spherical crosslinked dimethyl polysiloxane (product of Example 13) | 5.0 |

Preparation method

The components (1) to (4) were mixed and placed in a roll-on vessel, to prepare a roll-on deodorant.

The roll-on deodorant according to this Example was found to have fresh, free-flowing feeling during use on the skin, and an excellent deodorizing effect.

Example 40: Cleansing Powder

|  | Parts |
|---|---|
| (1) Soap powder | 40.0 |
| (2) N-myristoylmethyltauline sodium | 18.0 |
| (3) Myristic acid | 1.0 |
| (4) P.O.E. (20 mol) cetyl ether | 0.5 |
| (5) Perfume | 0.5 |
| (6) Magnesium aluminometasilicate (15%) and spherical polyMMA (5%) coated particulate starch (product of Example 14) | 15.0 |

Preparation method

After the components (1) to (5) were dissolved by heating to 70° C. in half the amount of the total weight thereof of purified water, (6) was dispersed in the solution, the dispersion was dried to form a powder by a spray drying treatment, and after controlling the particle size by sieving, the powder was filled in a vessel.

The cleansing powder according to this Example was found to have an excellent washing effect, and further, an excellent effect of removing sweaty odor from the skin surface.

Example 41: Lipstick

|  | Parts |
|---|---|
| (1) Magnesium aluminometasilicate (25.0%) and barium sulfate (10.0%) coated spherical cured bisphenol A-epichlorohydrin copolymer powder (product of Example 15) | 4.5 |
| (2) Red color No. 202 | 0.5 |
| (3) Red color No. 204 | 2.0 |
| (4) Red color No. 223 | 0.05 |
| (5) Ceresin | 15.0 |
| (6) Beeswax | 10.0 |
| (7) Cetyl alcohol | 5.0 |
| (8) Whale wax | 4.0 |
| (9) Carnauba wax | 1.0 |

-continued

|  | Parts |
|---|---|
| (10) Fluid paraffin | 20.95 |
| (11) Liquid lanolin | 20.0 |
| (12) Butylstearate | 15.0 |
| (13) Sorbitan sesquioleic acid ester | 2.0 |
| (14) Perfume | q.s. |
| (15) Antioxidant | q.s. |

A lipstick was obtained in a conventional manner.

The lipstick according to this Example was found to have a smooth extendability and a good cosmetic retentivity.

Example 42: Rouge

|  | Parts |
|---|---|
| (1) Magnesium aluminometasilicate (15.0%) coated plate-shaped polyethylene (product of Example 16) | 5.0 |
| (2) Talc | 80.0 |
| (3) Zinc stearate | 5.0 |
| (4) Rice starch | 10.0 |
| (5) Pigment | q.s. |
| (6) Perfume | q.s. |
| (7) Preservative | q.s. |

A rouge was obtained in a conventional manner.

The rouge according to this Example was found to have an excellent feeling during use and a good cosmetic retentivity.

Example 43: Eye-Shadow Stick

|  | Parts |
|---|---|
| (1) Ultramarine | 12.0 |
| (2) Talc | 4.0 |
| (3) Magnesium aluminometasilicate (28.0%) coated spherical nylon 6 (product of Example 17) | 5.0 |
| (4) Pearl pigment | 17.0 |
| (5) Carnauba wax | 10.0 |
| (6) Solid paraffin | 5.0 |
| (7) Lanolin derivative | 5.0 |
| (8) Squalane | 21.0 |
| (9) Glyceryl tri-2-ethylhexanoic acid ester | 20.0 |
| (10) Sorbitan sesquioleic acid ester | 1.0 |
| (11) Perfume | q.s. |

An eye shadow stick was obtained in a conventional manner.

The eye shadow stick according to this Example was found to have a smooth feeling during use and a good cosmetic retentivity.

Example 44: Eye Liner

|  | Parts |
|---|---|
| (1) Iron oxide (black) | 11.0 |
| (2) Magnesium aluminometasilicate (40.0%) coated fibrous cellulose powder (product of Example 18) | 5.0 |
| (3) Vinyl acetate resin emulsion | 43.0 |
| (4) Glycerine | 5.0 |
| (5) Polyoxyethylene (20 mol) sorbitan monooleic acid ester | 1.0 |
| (6) Carboxyethylenemethylcellulose (10% aqueous solution) | 15.0 |
| (7) Acetyltributyl citrate | 1.0 |
| (8) Purified water | 19.0 |

-continued

|  | Parts |
|---|---|
| (9) Perfume | q.s. |
| (10) Preservative | q.s. |

An eye liner was obtained in a conventional manner.

The eye liner according to this Example was found to have a smooth feeling during use and a good cosmetic retentivity.

Deodorant Containing Magnesium Aluminometasilicate Coated Composite Powder

Examples of deodorants containing magnesium aluminometasilicate coated composite powder are now described.

Example 45: Deodorant For Refrigerator

Magnesium aluminometasilicate (35%) coated spherical benzoguanamine resin (product of Example 19) was filled in a cloth bag, and contained in a plastic case provided with aeration holes, to obtain a deodorant for a refrigerator.

The following is a Comparative Example.

After 35% of magnesium aluminometasilicate and 65% of spherical benzoguanamine resin were mixed in a Henschel mixer, the mixture was filled in a cloth bag and contained in a plastic case provided with aeration holes, to obtain a deodorant for a refrigerator.

Next, the effect was confirmed by a practical use test.

The testees were 30 housewives, and 15 thereof were asked to use the deodorant for a refrigerator of Example 45 in refrigerators for domestic use, and the other 15 testees were asked to use the deodorant for a refrigerator of the Comparative Example for refrigerators for domestic use. The deodorizing effect after one hour was evaluated, and the results were as shown in Table 7.

As apparent from Table 7, the deodorant for a refrigerator of Example 45 exhibited a very strong deodorizing effect.

TABLE 7

|  | Example 45 | Comparative Example |
|---|---|---|
| No smell | 11 testees | 1 testee |
| Slight smell | 4 testees | 13 testees |
| Smell | 0 testees | 1 testee |

Example 46: Dew Formation Prevention Deodorant For Garbage Can

A predetermined amount of magnesium aluminometasilicate (38.0%) coated spherical polystyrene (product of Example 14) was filled in a cloth bag, and contained in a plastic case provided with aeration holes, to obtain a dew formation prevention deodorant for a garbage can.

The following is a Comparative Example.

Activated charcoal particles generally used for the deodorant for a refrigerator were filled, in the same amount as the coated powder of the Example, in a cloth bag and contained in a plastic case provided with aeration holes, to obtain a dew formation prevention deodorant for a garbage can.

Next, the effect was confirmed by a practical use test.

The testees were 20 housewives, and 10 thereof were asked to use the dew formation prevention deodorant for a garbage can of Example 46, and the other 10 testees were asked to use the dew formation prevention deodorant for a garbage can of the Comparative Example, in a plastic bucket having a required volume and prepared on our side. The plastic bucket was used exclusively for green garbage, and the filling with green garbage was stopped when about half the amount of the volume of the plastic bucket was filled, the dew formation prevention deodorant for a garbage can given to each testee was set at the lid portion of the plastic bucket, and the green garbage odor in the upper space of the plastic bucket and the amount of dew formation of water of the lid or wall surface of the plastic bucket 3 hours after the setting were evaluated by each individual.

The results are shown in Table 8 and Table 9.

As can be clearly seen from the Tables 8 and 9, the dew formation prevention deodorant for a garbage can of Example 46 had a deodorizing effect equal to that of activated charcoal, and an excellent dew formation prevention effect within the plastic bucket.

TABLE 8

|  | Example 46 | Comparative Example |
|---|---|---|
| No smell | 6 testees | 5 testees |
| Slight smell | 3 testees | 4 testees |
| Smell | 1 testees | 1 testee |

TABLE 9

|  | Example 46 | Comparative Example |
|---|---|---|
| No dew formation | 8 testees | 0 testees |
| Slight dew formation | 2 testees | 3 testees |
| Dew formed | 0 testees | 7 testees |

Example 47: Leather Insoles For Shoes

Magnesium aluminometasilicate (20%) and zinc oxide (10%) coated plate-shaped silicon dioxide (product of Example 20) was filled at the lower part of the upper skin of a leather insole, to obtain a leather insole for a shoe.

The following is a Comparative Example.

A mixture of magnesium aluminometasilicate and plate-shaped silicon dioxide mixed in a Henschel mixer at the same weight ratio as in Example 47 was filled at the lower part of the upper skin of leather insoles, to prepare leather insoles for shoes.

Next, the effect was confirmed by a practical use test.

The testees were 40 men who were aware of having foot odor. The testees wore the shoes with the leather insoles for shoes of Example 47 in one of the shoes, while wearing socks, and the leather insole of the Comparative Example in the other shoe. The shoes were taken off 2 hours later and the foot odor within the shoes and any stickiness caused by sweating were evaluated by each individual.

Table 10 shows the effect on the foot odor, and Table 11 the effect on the stickiness. As can be seen from Tables 10 and 11, the leather insole according to Example was found to have an excellent deodorizing effect and an excellent effect of inhibiting stickiness caused by sweating.

TABLE 10

|  | Example 47 | Comparative Example |
|---|---|---|
| No smell | 29 testees | 1 testee |
| Slight smell | 9 testees | 23 testees |
| Smell | 2 testees | 16 testees |

TABLE 11

|  | Example 47 | Comparative Example |
|---|---|---|
| No stickiness | 31 testees | 2 testees |
| Slightly sticky | 9 testees | 18 testees |
| Sticky | 0 testee | 20 testees |

Example 48: Paper Diaper

Magnesium aluminometasilicate (25%) coated particulate chitin (product of Example 21) was compounded into a water-absorptive polymer to obtain a paper diaper.

The paper diaper obtained was found to have an excellent deodorizing effect and did not become stiff even after use for a long time.

Example 49: Menstrual Product For Women

Magnesium aluminometasilicate (15%) and polytetrafluoroethylene (5%) coated silk fibroin powder (product of Example 22) was dispersed on the surface of a water-absorptive polymer, and a cloth was covered thereon to fix the powder and thus obtain a menstrual product for women.

The menstrual product according to this Example was found to have an excellent in deodorizing effect and did not become stiff during normal use.

Oral Hygiene Product Containing Magnesium Aluminometasilicate Coated Composite Powder Examples of oral hygiene products containing magnesium aluminometasilicate coated powder are now described.

Example 50: Toothpaste

|  |  | Parts |
|---|---|---|
| (1) | Magnesium aluminometasilicate (22.0%) coated spherical chitosan (product of Example 23) | 40.0 |
| (2) | Glycerine | 15.0 |
| (3) | Carboxymethylcellulose | 0.8 |
| (4) | Sodium lauryl sulfate | 1.5 |
| (5) | Saccharin sodium | 0.15 |
| (6) | Perfume | 1.0 |
| (7) | Purified water | 56.55 |

The preparation was performed in a conventional manner.

The following is a Comparative Example.

|  |  | Parts |
|---|---|---|
| (1) | Magnesium aluminometasilicate | 6.0 |
| (2) | Polytetrafluoroethylene | 2.0 |
| (3) | Spherical chitosan | 32.0 |
| (4) | Glycerine | 15.0 |
| (5) | Carboxymethylcellulose | 0.8 |
| (6) | Sodium lauryl sulfate | 1.5 |
| (7) | Saccharin sodium | 0.15 |
| (8) | Perfume | 1.0 |
| (9) | Purified water | 56.55 |

Next, the effect was confirmed by a practical use test.

Thirty testees were asked to use the toothpaste of the present invention, and the feeling during use thereof was determined. Each testee was asked to use the toothpastes of Example 50 and the Comparative Example alternately, 3 times each (brushing time 3 minutes each), and the feeling during use was evaluated by each individual.

The results are shown in Table 12.

As apparent from Table 12, the toothpaste of Example 50 had a better feeling during use than the Comparative Example. Also, the dispersion stability in the recipe thereof was good.

TABLE 12

|  | Example 50 | Comparative Example |
|---|---|---|
| Very smooth | 22 testees | 0 testees |
| Smooth | 6 testees | 1 testee |
| Slightly rough | 1 testee | 6 testees |
| Rough | 1 testee | 16 testees |
| Very rough | 0 testees | 7 testees |

Example 51: Wettable Toothpaste

|  | Parts |
|---|---|
| (1) Magnesium aluminometasilicate (30.0%) and hydroxyapatite (10.0%) coated particulate silicon dioxide (product of Example 24) | 60.0 |
| (2) Heavy calcium carbonate | 10.0 |
| (3) Light calcium carbonate | 10.0 |
| (4) Glycerine | 15.0 |
| (5) Sodium lauryl sulfate | 1.5 |
| (6) Purified water | 2.3 |
| (7) Perfume | 1.2 |
| (8) Sweetener | q.s. |
| (9) dye | q.s. |

Preparation method

Components (6), (8) and (9) were dissolved in purified water (aqueous portion), and the other components were mixed and added to the aqueous portion, followed by a thorough mixing by a blender to obtain a wettable toothpaste.

The following is a Comparative Example.

|  | Parts |
|---|---|
| (1) Magnesium aluminometasilicate | 18.0 |
| (2) Hydroxyapatite | 6.0 |
| (3) Particulate silicon dioxide | 36.0 |
| (4) Heavy calcium carbonate | 10.0 |
| (5) Light calcium carbonate | 10.0 |
| (6) Glycerine | 15.0 |
| (7) Sodium lauryl sulfate | 1.5 |
| (8) Purified water | 2.3 |
| (9) Perfume | 1.2 |
| (10) Sweetener | q.s. |
| (11) Dye | q.s. |

Next, the effect was confirmed by a practical use test.

Twenty testees were used to determine the deodorizing effect of the wettable toothpaste according to this Example. Each testee was asked to use the wettable toothpastes of Example 51 and the Comparative Example, in the morning and in the evening for 3 days each over a period of 6 days, and the deodorizing effect during use was evaluated by each individual.

The test results are shown in Table 13.

From Table 13, it is clear that the wettable toothpaste of Example 51 has a greater deodorizing effect than that of the Comparative Example; and that the feeling during use thereof was good.

TABLE 13

|  | Example 51 | Comparative Example |
|---|---|---|
| No smell | 6 testees | 1 testee |
| Strong deodorizing effect | 11 testees | 5 testees |
| Good deodorizing effect | 2 testees | 10 testees |
| Slight deodorizing effect | 1 testee | 4 testees |
| No deodorizing effect | 0 testees | 0 testees |

Example 52: Mouthwash

|  | Parts |
|---|---|
| (1) Magnesium aluminometasilicate (33.0%) coated particulate cellulose (product of Example 25) | 1.5 |
| (2) Sodium hydrogen carbonate | 0.8 |
| (3) Thymol | 0.1 |
| (4) Peppermint oil | 0.1 |
| (5) Ethanol | 38.0 |
| (6) Glycerine | 14.0 |
| (7) Aqueous cinnamon | 45.5 |

The components (1) to (7) were mixed to obtain a mouthwash, and the mouthwash according to this Example was found to have an excellent deodorizing effect.

Example 53: Powder Toothpaste

|  | Parts |
|---|---|
| (1) Magnesium aluminometasilicate (20.0%) and silicon dioxide (20.0%) coated fibrous nylon 12 (product of Example 26) | 50.0 |
| (2) Heavy calcium carbonate | 22.5 |
| (3) Light calcium carbonate | 22.5 |
| (4) Sodium lauryl sulfate | 3.8 |
| (5) Perfume | 1.2 |
| (6) Sweetener | q.s. |
| (7) Dye | q.s. |

The components (1) to (7) were mixed to obtain a powder toothpaste. This product was found to have an excellent abrasive force, deodorizing effect, and good feeling during use.

The present invention is constituted as described above, and has the effects as described below.

According to the magnesium aluminometasilicate coated composite powder of the present invention since magnesium metasilicate aluminate is coated on the surface of a powdery nucleus, the adsorption effect can be greatly improved.

According to the skin treatment agent of the present invention, since magnesium aluminometasilicate coated composite powder is contained therein, the dispersion stability in the product can be improved to effectively exhibit a skin waste adsorption capacity, water absorption and dissipation characteristic, deodorizing effect, and cosmetic retentivity effect, and the extendability on skin can be also improved.

According to the deodorant of the present invention, since magnesium aluminometasilicate coated composite powder is contained therein, the deodorizing effect and the dew formation prevention effect can be improved.

According to the oral composition of the present invention, since magnesium aluminometasilicate coated powder is contained therein, the dispersion stability, abrasive force, and deodorizing effect in the product can be improved.

We claim:

1. A composite powder which comprises magnesium aluminometasilicate and optionally at least one other powder selected from the group consisting of organic powders of polyamide resin, polyolefin resin, polystyrene, polyester resin, acrylic resin, epoxy resin, fluorine type resin, silicone type resin, phenol resin, vinyl resin, vinylidene resin, polyurethane resin, natural rubber, synthetic rubber, chitin, chitosan, fibroin, keratin, and cellulose, and inorganic powders of talc, kaolin, mica, titanium dioxide, zinc white, zirconium oxide, anhydrous silicic acid, barium sulfate, iron oxide, mica, aluminum hydroxide chloride, calcium phosphate, and calcium secondary phosphate, coated on a surface of a core powder, said composite powder being produced by dry mixing the core powder and magnesium aluminometasilicate and the optional powder.

2. A composite powder as claimed in claim 1, wherein the core powder is an organic or inorganic powder having an average particle size of 0.1 to 500 μm.

3. A composite powder as claimed in claim 1, wherein the magnesium aluminometasilicate powder has an average particle size one-fifth or less of the average particle size of the above-mentioned core powder.

4. A skin treatment agent which includes the magnesium aluminometasilicate coated composite powder of claim 1.

5. A skin treatment agent as claimed in claim 4, wherein the core powder is an organic or inorganic powder having an average particle size of 0.1 to 500 μm.

6. A skin treatment agent as claimed in claim 4, wherein the magnesium aluminometasilicate powder has an average particle size one-fifth or less of the average particle size of the above-mentioned core powder.

7. A deodorant which includes the magnesium aluminometasilicate coated composite powder of claim 1.

8. A deodorant as claimed in claim 7, wherein the core powder is an organic or inorganic powder having an average particle size of 0.1 to 500 μm.

9. A deodorant as claimed in claim 7, wherein the magnesium aluminometasilicate powder has an average particle size one-fifth or less of the average particle size of the above-mentioned core powder.

10. An oral hygiene product which includes the magnesium aluminometasilicate coated composite powder of claim 1.

11. An oral hygiene product as claimed in claim 10, wherein the core powder is an organic or inorganic powder having an average particle size of 0.1 to 500 μm.

12. An oral hygiene product as claimed in claim 10, wherein the magnesium aluminometasilicate powder has an average particle size one-fifth or less of the average particle size of the above-mentioned core powder.

13. A composite powder as claimed in claim 1, wherein the core powder is at least one powder selected from the group consisting of polyamide resin, polyolefin resin, polystyrene resin, polyester resin, acrylic resin, epoxy resin, fluorine resin, silicone resin, phenol resin, vinyl resin, vinylidene resin, polyurethane resin, natural rubber, synthetic rubber, chitin, chitosan, fibroin, keratin and cellulose.

* * * * *